United States Patent
Harvey et al.

(10) Patent No.: US 10,711,215 B1
(45) Date of Patent: Jul. 14, 2020

(54) RENEWABLE DIOXOLANE-BASED GASOLINE-RANGE FUELS AND DIESEL ADDITIVES

(71) Applicant: The Government of the United States of America as Represented by the Secretary of the Navy, Arlington, VA (US)

(72) Inventors: Benjamin G. Harvey, Ridgecrest, CA (US); Heather A. Meylemans, Ridgecrest, CA (US)

(73) Assignee: The Government of the United States of America as represented by the Secretary of the Navy, Washington, DC (US)

( * ) Notice: Subject to any disclaimer, the term of this patent is extended or adjusted under 35 U.S.C. 154(b) by 256 days.

(21) Appl. No.: 14/834,071

(22) Filed: Aug. 24, 2015

Related U.S. Application Data

(60) Provisional application No. 62/043,129, filed on Aug. 28, 2014.

(51) Int. Cl.
| | | |
|---|---|---|
| *C10L 10/10* | (2006.01) | |
| *C10L 1/18* | (2006.01) | |
| *C10L 1/02* | (2006.01) | |
| *C07D 317/12* | (2006.01) | |
| *C10L 1/185* | (2006.01) | |

(52) U.S. Cl.
CPC ............ *C10L 10/10* (2013.01); *C07D 317/12* (2013.01); *C10L 1/023* (2013.01); *C10L 1/18* (2013.01); *C10L 1/1855* (2013.01); *C10L 2200/0469* (2013.01); *C10L 2270/023* (2013.01); *C10L 2290/02* (2013.01); *C10L 2290/08* (2013.01); *C10L 2290/26* (2013.01); *C10L 2290/543* (2013.01)

(58) Field of Classification Search
None
See application file for complete search history.

(56) References Cited

U.S. PATENT DOCUMENTS

| | | | |
|---|---|---|---|
| 2,509,874 A | 5/1950 | Mcateer | |
| 4,390,345 A * | 6/1983 | Somorjai | C10L 1/14 44/352 |
| 2010/0108567 A1* | 5/2010 | Medoff | C10G 3/00 208/49 |
| 2014/0238841 A1* | 8/2014 | Kawamura | C07C 29/80 203/37 |

OTHER PUBLICATIONS

Zhang, Simpler is Better: High-Yield and Potential Low-Cost Biofuels Production Through Cell-Free Synthetic Pathway Biotransformation (SyPaB), ACS Catal. 2011, 998-1009.*
Schlaf, Selective deoxygenation of sugar polyols to a,w-diols and other oxygen content reduced materials—a new challenge to homogeneous ionic hydrogenation and hydrogenolysis catalysis, Dalton Trans 2006, 4645-4653.*
Broekhuis et al., Recovery of Propylene Glycol from Dilute Aqueous Solutions via Reversible Reaction with Aldehydes, Dec. 1993.*
Ewing et al., Optical and geometrical isomers of some fatty acids with vicinal hydroxy groups, Canadian Journal of Chemistry, vol. 45, 1259 (19670.*
Organic Synthesis (Chapter 7), pp. 587-622, 2010.*

* cited by examiner

*Primary Examiner* — Sharmila G Landau
*Assistant Examiner* — Stephen M Chong
(74) *Attorney, Agent, or Firm* — Naval Air Warfare Center Weapons Division; Charlene A. Haley; Matthew D. Pangallo

(57) ABSTRACT

A method to generate dioxolanes from renewable feedstocks, and more specifically, these oxygenated hydrocarbons can be used as gasoline-range fuels and diesel additives.

6 Claims, 4 Drawing Sheets

RENEWABLE DIOXOLANE-BASED GASOLINE-RANGE FUELS AND DIESEL ADDITIVES

CROSS-REFERENCE TO RELATED APPLICATIONS

This is a non-provisional patent application, claiming the benefit of, parent application Ser. No. 62/043,129 filed on Aug. 28, 2014, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods to generate dioxolanes from renewable feedstocks, and more specifically, these oxygenated hydrocarbons can be used as gasoline-range fuels and diesel additives.

BRIEF DESCRIPTION OF THE DRAWING(S)

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to methods of synthesizing dioxolanes from vicinal diols using heterogeneous catalysts under various dehydrating conditions. The diols can be readily generated from biomass allowing for the synthesis of renewable gasoline and diesel additives.

The invention describes a method to efficiently convert renewable vicinal diols (e.g. 2,3-butanediol, 1,2-propanediol, but not limited to) to dioxolanes that have applications as gasoline-range fuels and diesel oxygenates. These fuels have exceptional octane numbers (>90) coupled with lower solubilities in water, and higher flashpoints than typical oxygenates such as ethanol, butanol, and MTBE. Moreover these dioxolanes are fully miscible with diesel fuel and can be used to reduce particle emissions. Butanediol can be produced from biomass or syngas (primarily CO derived from biomass or other sources). The process to generate the dioxolanes utilizes cheap and readily available heterogeneous catalysts that allow for simple separation of the dioxolanes from reaction mixtures, while the catalysts can be used for multiple cycles without degradation. The process can be conducted at modest temperatures and pressures with entraining solvents, hydrophilic membranes, or desiccants. U.S. Pat. No. 2,509,874 describes the synthesis of acetals from vicinal diols using sulfuric acid.

Figure 1:
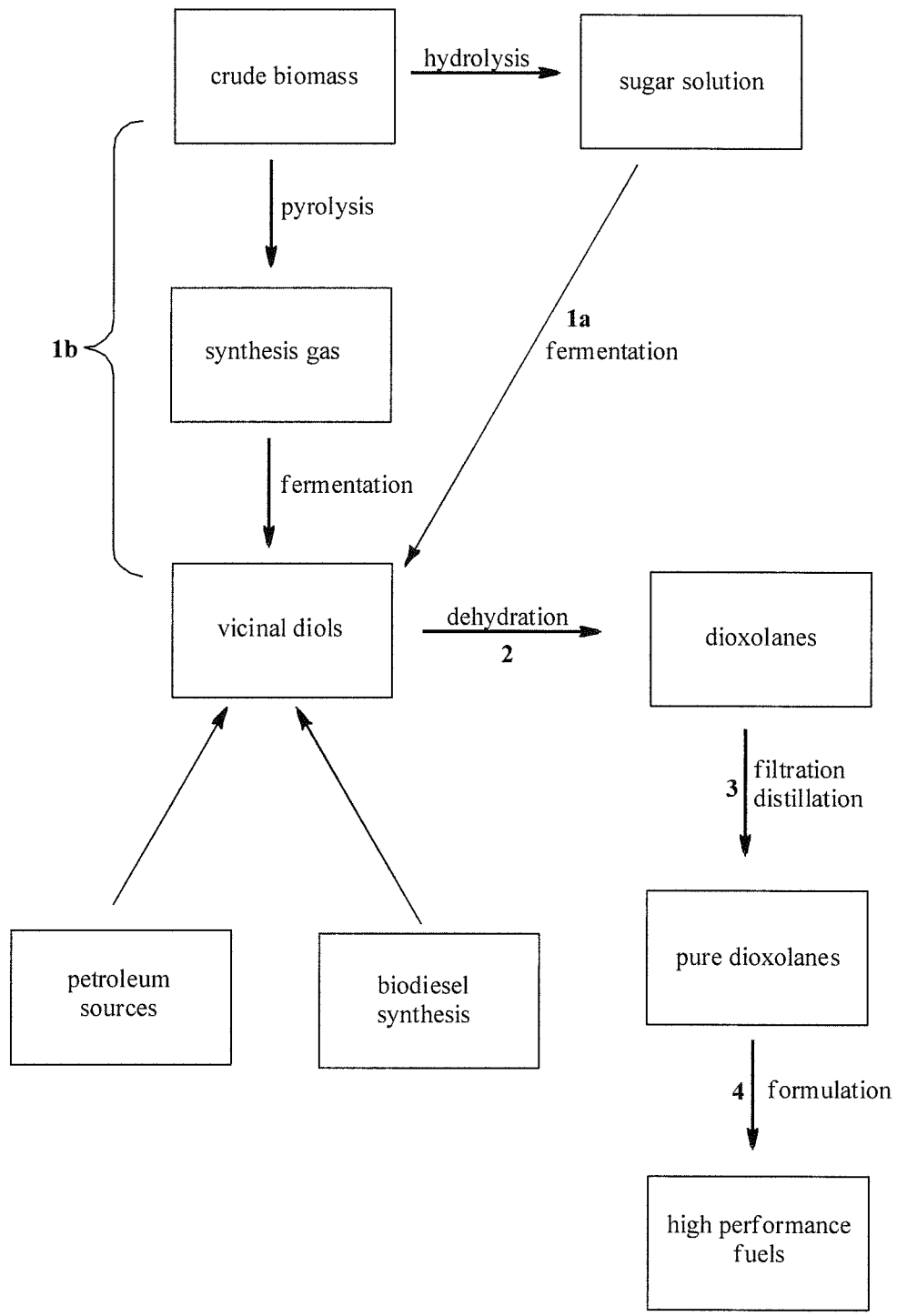
FIG. 1 is a flow chart showing dehydration of vicinal diols to generate dioxolanes, according to embodiments of the invention.
Figure 2:
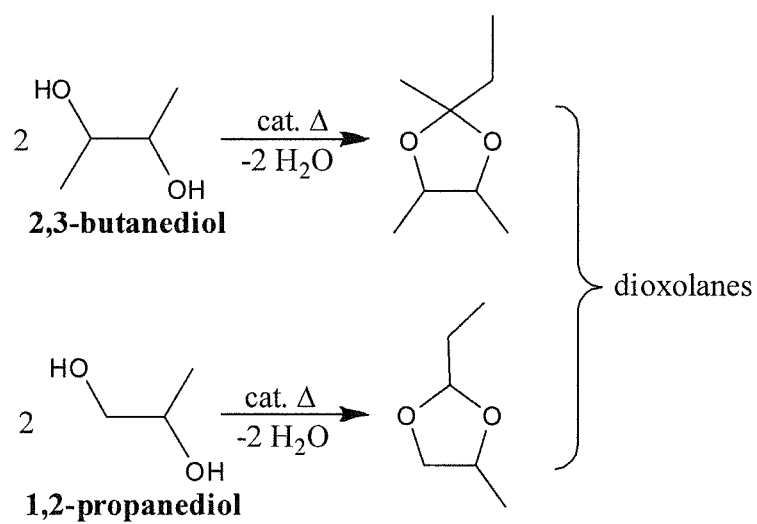
FIG. 2 is a chemical schematic showing dehydration of vicinal diols to generate dioxolanes, according to embodiments of the invention.

1. Vicinal diols including, but not limited to, 2,3-butanediol and 1,2-propanediol are produced by fermentation of biomass-derived sugars or from biomass-derived syngas. (see FIGS. 1 and 2 showing dehydration of vicinal diols to generate dioxolanes)

2. Vicinal diols are allowed to react with a solid acid catalyst at elevated temperature.

Water generated in the process can be sequestered by, but not limited to:
  a. Azeotropic distillation
  b. Vapor phase removal via a hydrophilic membrane
  c. Use of a desiccant
  d. A combination of steps a-c.

3. The product dioxolanes are separated from the heterogeneous catalyst by filtration or decantation and distilled to generate pure dioxolanes.

4. Dioxalanes are blended with petroleum-based or renewable fuels.

1a. 2,3-butanediol is generated by fermentation of sugar solutions derived from biomass, including, but not limited to, lignocellulosic, cellulosic, and hemicellulosic feedstocks. The fermentation can be accomplished with a variety of organisms including, but not limited to, *Klebsiella oxytoca, Enterobacter aerogenes, Bacillus polymyxa*, and *Bacillus licheniformis*.

1b. Vicinal diols can also be generated by fermentation of CO from synthesis gas generated from biomass, municipal waste, industrial operations (steel production), etc.

Pure diols or aqueous solutions of diols can be used for subsequent steps. 1,2-propanediol can be generated from glycerol through dehydration to acetol followed by catalytic hydrogenation. 1,2-propanediol can also be derived from biomass through a fermentation process.

2. Vicinal diols are allowed to react with heterogeneous acid catalysts. Catalysts include cation exchange resins such as Amberlyst, Nafion, polyphosphoric acid, as well as metal oxides, zeolites, and supported Bronsted acids. The heterogeneous mixture is heated (temperature depends on the required rate and catalyst) in the range from ambient temperature up to 150 degrees C. The reaction is driven to completion by sequestration of water by one of the methods listed below:

a. A solvent that forms a low-boiling azeotrope with water can be used to selectively remove water from the reaction mixture. Examples include benzene, toluene and cyclohexane. The mixture is heated to the reflux temperature of the azeotrope, the azeotropic mixture is collected, and the water is removed by draining the lower layer of the biphasic mixture. The entraining solvent is continuously recycled to the reaction mixture.

b. Hydrophilic membranes are used to remove water as it is formed. The reaction is conducted without a solvent at elevated temperature and water is removed from a porous tubular reactor containing a membrane layer that selectively removes water from the vapor.

c. A desiccant including molecular sieves, $CaCl_2$, $MgSO_4$, and related materials can be utilized either directly in the reaction mixture or be placed in a tubular reactor to capture the water from the gas phase.

3. The heterogeneous catalyst is separated by simple decantation or filtration and recycled for further use. Dioxolanes are purified by distillation. In the case where a solvent is utilized, the solvent can be recycled for additional runs.

4. Dioxolanes are blended with conventional gasoline or diesel fuels. In the case of gasoline, they can provide significant octane improvement, while blending with diesel fuels can significantly reduce the amount of unburned hydrocarbons emitted, particularly carcinogenic polyaromatic hydrocarbons. In embodiments, the dioxolanes are mixed with renewable fuels (e.g. hydrogenated terpenes) to generate high octane fuels.

Example 1. Synthesis of Dioxolanes from 2,3-butanediol

In a typical preparative synthesis, 2,3-butanediol (1500 g), and Amberlyst-15 (20 g) were placed in a 2-liter, three-necked flask equipped with a stir bar, thermometer, and a 15 in. vacuum jacketed Vigreux column. The pressure was reduced to 123 Torr and the internal temperature of the flask was increased to 115+/−5° C. Products were collected in a flask over the course of several hours and allowed to phase separate. 1345 g of distillate were collected (90%). The distillate was transferred to a separatory funnel and the lower aqueous layer was separated. The top layer was washed twice with water and then dried over MgSO4. Methyl ethyl ketone was removed by fractional distillation to give a mixture of dioxolanes (typical yield 65-75%). The aqueous layer contained a significant quantity of MEK which could be purified to ca. 90% purity by azeotropic distillation.

Figure 3:
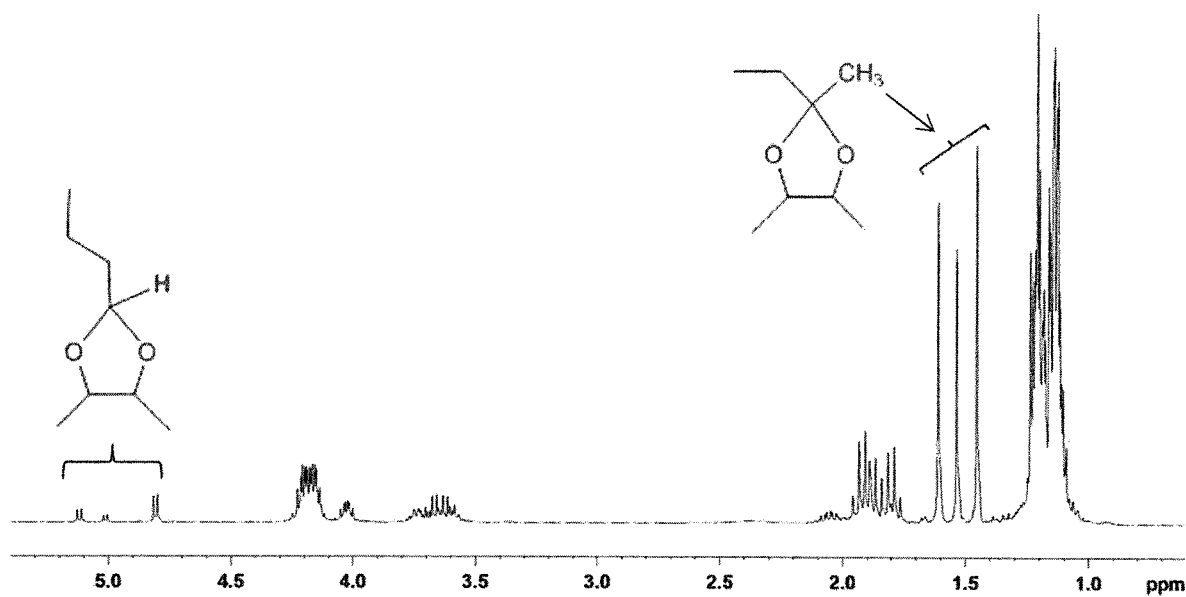
FIG. 3 is a graph showing a $^1$H NMR spectrum of the dioxolane fraction, according to embodiments of the invention.

FIG. 3. Representative $^1$H NMR spectrum of the dioxolane fraction. The main components of the dioxolane fraction (three stereoisomers of TMED) can be monitored via the distinctive methyl groups centered at ~1.5 ppm. The three stereoisomers of 2-propyl-4,5-dimethyldioxolane can be monitored via the broad doublets between 4.8 and 5.1 ppm.

Figure 4:
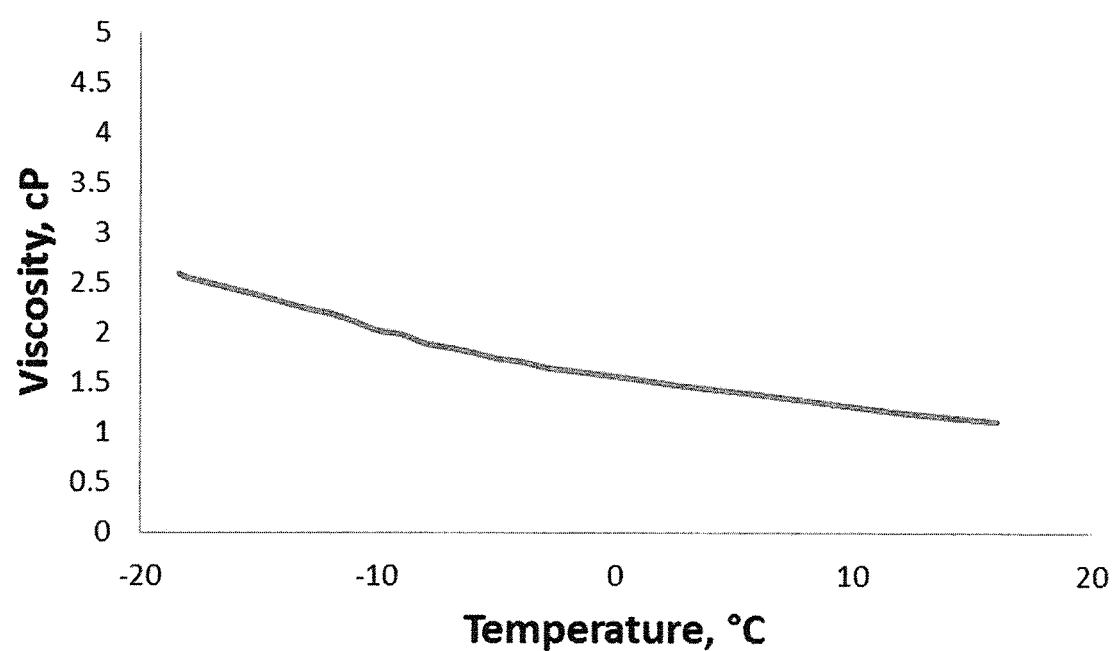
FIG. 4 is a graph showing shear viscometry data for a typical 2,3-butanediol derived dioxolane mixture, according to embodiments of the invention.

FIG. 4. Shear viscometry data for a typical 2,3-butanediol derived dioxolane mixture.

TABLE 1

Fuel Properties of Dioxolanes Prepared from 2,3-Butanediol

| Property | Value |
| --- | --- |
| Density | 0.902 g/mL |
| Volumetric Net Heat of Combustion | 29.0 MJ/L |
| Water Miscibility | <0.1 g/100 mL |
| Flashpoint | 32° C. |
| Research Octane Number | 93.5 |
| Motor Octane Number | 86.7 |
| (R + M)/2-Antiknock Index | 90.1 |

Embodiments of the invention generally relate to methods for converting crude biomass to high octane gasoline-range fuels or diesel fuel additives including, providing at least one crude biomass source, hydrolyzing the biomass source to produce a sugar solution, fermenting the sugar solution to produce vicinal diols, dehydrating the vicinal diols with at least one heterogeneous acid catalyst via a reactive distillation process to produce dioxolanes and other dehydration products including ketones and aldehydes, purifying the dioxolanes by phase separating and distilling to produce pure dioxolanes, and using pure dioxolanes directly as fuels or blending the pure dioxolanes with petroleum-based or renewable fuels to produce high octane gasoline-range fuels or oxygenated diesel fuels.

In embodiments, the vicinal diols are selected from the group consisting of 2,3-butanediol, and/or 1,2-propanediol. Further embodiments include dehydrating the vicinal dials in the presence of added ketones to generate dioxolane mixtures. In embodiments, the ketone is acetone and resulting dioxolane mixtures includes 2,2,4,5-tetramethyl-1,3-dioxolane. In embodiments, the heterogeneous catalyst is reuseable and is selected from the group consisting of solid acid catalysts, polyphosphoric acid, metal oxides, zeolites, cation exchange resins including Amberlyst and Nafion, and Brönsted acids supported on silica, alumina, polymers, any other support material to all embodiments and aspect of the inventions herein, and any combination thereof. Further embodiments include the use of solvents, vapor phase removal via hydrophilic membranes, or use of desiccants, azeotropic distillation, or combination thereof to remove any water generated during the catalyzed dehydration step. In embodiments, other dehydration products are purified by distillation.

In embodiments, the crude biomass is selected from the group consisting of lignocellulosic, cellulosic, hemicellulosic feedstocks, or any combination thereof. In embodiments, the fermenting uses a variety of organisms selected from the group consisting of *Klebsiella oxytoca, Enterobacter aerogenes, Bacillus polymyxa*, and *Bacillus licheniformis*, or any combination thereof.

Another aspect of the invention generally relates to methods for converting crude biomass to high octane gasoline-range fuels or diesel fuel additives including, providing at least one crude biomass source, pyrolyzing the biomass source to produce a synthesis gas, fermenting the synthesis gas to produce CO to then produce vicinal diols, dehydrating the vicinal diols with at least one heterogeneous acid catalyst via a reactive distillation process to produce dioxolanes and other dehydration products including ketones and aldehydes, purifying the dioxolanes by phase separating and distilling to produce pure dioxolanes, and using pure dioxolanes directly as fuels or blending the pure dioxolanes with petroleum-based or renewable fuels to produce high octane gasoline-range fuels or oxygenated diesel fuels. In embodiments, the vicinal diols are selected from the group consisting of 2,3-butanediol, and/or 1,2-propanediol. In embodiments, the heterogeneous catalyst is reuseable and is selected from the group consisting of solid acid catalysts, polyphosphoric acid, metal oxides, zeolites, cation exchange resins including Amberlyst and Nafion, and Brönsted acids supported on silica, alumina, polymers, and any combination thereof. Further embodiments include the use of solvents, vapor phase removal via hydrophilic membranes, or use of desiccants, azeotropic distillation, or combination thereof to remove any water generated during the catalyzed dehydration step. In embodiments, the crude biomass is selected from the group consisting of lignocellulosic, cellulosic, hemicellulosic feedstocks, or any combination thereof. In embodiments, the fermenting uses a variety of organisms selected from the group consisting of *Klebsiella oxytoca, Enterobacter aerogenes, Bacillus polymyxa*, and *Bacillus licheniformis*, or any combination thereof.

Another aspect of the invention relates to methods for converting vicinal diols to high octane gasoline-range fuels or diesel fuel additives including, providing vicinal diols from a petroleum source or through biodiesel synthesis, dehydrating the vicinal diols with at least one heterogeneous acid catalyst via a reactive distillation process to produce dioxolanes and other dehydration products including ketones and aldehydes, purifying the dioxolanes by phase separating and distalling to produce pure dioxolanes, and using pure dioxolanes directly as fuels or blending the pure dioxolanes with petroleum-based or renewable fuels to produce high octane gasoline range fuels or oxygenated diesel fuels. In embodiments, the vicinal diols are selected from the group consisting of 2,3-butanediol, and/or 1,2-propanediol. In embodiments, the heterogeneous catalyst is reuseable and is selected from the group consisting of solid acid catalysts, polyphosphoric acid, metal oxides, zeolites, cation exchange resins including Amberlyst and Nafion, and Brönsted acids supported on silica, alumina, polymers, and any combination thereof. Further embodiments include the use of solvents, vapor phase removal via hydrophilic membranes, or use of desiccants, azeotropic distillation, or combination thereof to remove any water generated during the catalyzed dehydration step. In other aspects of the invention, the fuels and fuel additives are embodiments of the invention.

Prophetic Examples

The following prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various teaus of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for converting crude biomass to high octane gasoline-range fuels or diesel fuel additives, consisting of:
   providing at least one crude biomass source; hydrolyzing said biomass source to produce a sugar solution; fermenting said sugar solution to produce vicinal diols;
   dehydrating said vicinal diols with at least one heterogeneous acid catalyst and removing water with a reactive distillation process to produce dioxolanes and other dehydration products including ketones and aldehydes, wherein the dehydrating consists of the vicinal diols and the at least one heterogeneous acid catalyst;
   purifying said dioxolanes by phase separating and distilling to produce pure dioxolanes; and
   using said pure dioxolanes directly as fuels or blending said pure dioxolanes with petroleum-based or renewable fuels to produce high octane gasoline-range fuels or oxygenated diesel fuels.

2. The method according to claim 1, wherein said vicinal diols are selected from the group consisting of 2,3-butanediol, 1,2-propanediol, and combinations thereof.

3. The method according to claim 1 wherein said heterogeneous catalyst is reuseable and is selected from the group consisting of solid acid catalysts, polyphosphoric acid, metal oxides, zeolites, cation exchange resins including Amberlyst and Nafion, and Brönsted acids supported on silica, alumina, polymers, and any combination thereof.

4. The method according to claim 1, wherein said crude biomass is selected from the group consisting of lignocellulosic, cellulosic, hemicellulosic feedstocks, or any combination thereof.

5. The method according to claim 1, wherein said fermenting uses a variety of organisms selected from the group consisting of *Klebsiella oxytoca, Enterobacter aerogenes, Bacillus polymyxa*, and *Bacillus licheniformis*, or any combination thereof.

6. A method for making a blended fuel, consisting of:
   mixing 2,3-butanediol with a polystyrene based ion exchange resin under vacuum at a pressure of about 123 Torr and a temperature of about 115° C., thereby forming a mixture of methyl ethyl ketone and 2-propyl-4,5-dimethyldioxolane;
   phase separating the mixture, thereby forming a distillate layer and an aqueous layer;
   washing the distillate layer with water and drying the distillate layer over $MgSO_4$, thereby forming 2-propyl-4,5-dimethyldioxolane;
   purifying the 2-propyl-4,5-dimethyldioxolane, thereby forming purified 2-propyl-4,5-dimethyldioxolane; and
   adding the purified 2-propyl-4,5-dimethyldioxolane to a fuel, thereby forming a blended fuel.

* * * * *